United States Patent [19]

Cotter

[11] 4,136,122

[45] Jan. 23, 1979

[54] SEPARATION OF 2,6-DICHLOROBENZALDEHYDE FROM ISOMERIC MIXTURES

[75] Inventor: Byron R. Cotter, Grand Island, N.Y.

[73] Assignee: Hooker Chemicals & Plastics Corp., Niagara Falls, N.Y.

[21] Appl. No.: 888,594

[22] Filed: Mar. 20, 1978

[51] Int. Cl.$^2$ .............................................. C07C 45/24
[52] U.S. Cl. ................................................. 260/599
[58] Field of Search ........................................ 260/599

[56] References Cited

U.S. PATENT DOCUMENTS 3,524,885  8/1970  Deinet .................................. 260/599

FOREIGN PATENT DOCUMENTS 1214916  12/1970  United Kingdom.

OTHER PUBLICATIONS

Reich et al., Chem. Abs., vol. 12 (1918) 580.

*Primary Examiner*—Bernard Helfin
*Attorney, Agent, or Firm*—Peter F. Casella; William J. Crossetta, Jr.; Arthur S. Cookfair

[57] ABSTRACT

A process for the separation of 2,6-dichlorobenzaldehyde from an isomeric mixture of dichlorobenzaldehyde comprises dissolving the isomeric mixture in a water-immiscible organic solvent, contacting the solvent with an aqueous sodium bisulfite solution, separating the aqueous solution and recovering 2,6-dichlorobenzaldehyde from the organic solvent.

12 Claims, No Drawings

SEPARATION OF 2,6-DICHLOROBENZALDEHYDE FROM ISOMERIC MIXTURES

BACKGROUND OF THE INVENTION

This invention relates to a process for the separation of 2,6-dichlorobenzaldehyde from isomeric mixtures of dichlorobenzaldehydes. The product, 2,6-dichlorobenzaldehyde is useful as an intermediate in the preparation of various chemical products, and in particular as an intermediate in the preparation of herbicides, insecticides and dyestuffs.

Dichlorobenzaldehydes may be prepared by various known methods. In some methods of preparation, the product is formed as an isomeric mixture. For example, dichlorobenzaldehydes may be prepared by ring chlorination of toluene to form a mixture of dichlorotoluenes, followed by photochlorination of the mixture to form the corresponding dichlorobenzalchlorides and hydrolyzing, for example with sulfuric acid. The product is typically an isomeric mixture of 2,3-, 2,4-, 2,5-, 2,6-, and 3,4-, dichlorobenzaldehydes. It is a primary object of this invention to provide a simple and effective method for the separation of 2,6-dichlorobenzaldehyde from an isomeric mixture of dichlorobenzaldehydes.

SUMMARY OF THE INVENTION

In accordance with this invention 2,6-dichlorobenzaldehyde is separated from an isomeric mixture of dichlorobenzaldehydes by dissolving the isomeric mixture in a water-immiscible organic solvent; contacting the solvent with an aqueous sodium bisulfite solution; separating the resultant organic and aqueous phases; and recovering the organic solvent containing 2,6-dichlorobenzaldehyde. The dissolved product may then be recovered from the organic solvent by known methods, for example by evaporation. The treatment with organic solvent and aqueous sodium bisulfite may be repeated if further purification of the 2,6-dichlorobenzaldehyde is desired.

The organic solvent employed must be a solvent for dichlorobenzaldehydes, substantially water-immiscible and chemically inert with respect to aqueous sodium bisulfite and the dichlorobenzaldehydes, and preferably have a boiling point above about 90° Celsius. Suitable solvents include, for example, various liquid aliphatic and aromatic hydrocarbons such as toluene, xylene, heptane, octane, methylcyclohexane, and the like, ethers, and substituted hydrocarbons, especially chlorinated organic solvents, such as chlorobenzene, trichloroethylene, tetrachloroethylene, and the like. A preferred solvent is toluene.

The organic solvent containing dissolved isomers of dichlorobenzaldehyde is mixed with aqueous sodium bisulfite, preferably at an elevated temperature. It is preferred to maintain the temperature of the mixture below boiling point of the mixture and above the temperature at which substantial crystallization will occur. Based on these considerations, the effective temperature range is typically about 50° to about 100° Celsius, and most preferably about 70° to about 95° Celsius.

The strength of the sodium bisulfite solution employed may vary considerably but will typically be in the range of about 1.0 to about 5.0 molar. The proportion of aqueous sodium bisulfite employed may also vary considerably, depending on the amount of isomeric mixture dissolved in the organic solvent and the strength, e.g. molarity of the aqueous sodium bisulfite. Typically, for a mixture in the range of about 15 to about 50 percent by weight of dichlorobenzaldehyde isomers dissolved in an organic solvent, aqueous sodium bisulfite, for example, leaving a strength of about 1.0 to about 5.0 M, may be employed in a proportion of about 0.5 or less to about 5.0 parts by weight or more per part by weight of organic solution. However, the proportions may be varied considerably, depending on the percentage of dissolved isomers present and the molarity of the aqueous sodium bisulfite as well as the particular organic solvent and temperatures employed. It is preferred to carry out the process at atmospheric pressures, however, subatmospheric or super-atmospheric pressures may be employed if desired.

The separation of 2,6-dichlorobenzaldehyde in accordance with this invention may be carried out as a simple batch process which may be repeated one or more times to provide further purification, or may be carried out as a continuous process, such as by counter-current extraction utilizing conventional techniques.

The following specific examples are provided to further illustrate this invention and the manner in which it may be carried out. It will be understood, however, that the specific details given in the examples have been chosen for purpose of illustration and are not to be construed as a limitation on the invention. In the examples, unless otherwise indicated, all parts and percentages are by weight and all temperatures are in degrees Celsius.

EXAMPLE 1

A mixture of dichlorobenzaldehyde isomers consisting of 2.95 parts of 2,6-dichlorobenzaldehyde and 6.38 parts of a mixture of 2,3-, 2,4-, and 2,5-dichlorobenzaldehydes was dissolved in 26 parts of toluene. To the solution was added 0.664 parts of 2,4-dichlorotoluene, to serve as a gas-chromatographic internal standard for subsequent analysis. A solution of 10 parts of sodium bisulfite in 30 parts of water was added with mixing. The resultant mixture was heated and maintained at about 85° C. for about 30 minutes, with agitation and then allowed to settle, forming an aqueous phase and an organic solvent phase. Analysis of both phases indicated a preferential extraction of the 2,3-, 2,4-, and 2,5- isomers into the aqueous phase, with 70% of the starting 2,6- isomer and 38% of the starting mixture of other isomers remaining in the toluene.

EXAMPLE 2

The procedure of Example 1 was repeated except that temperature during extraction was maintained at about 60° C. Analysis of the toluene phase indicated about 33% of the starting 2,6- isomer and about 10.2% of the starting mixture of other isomers remained in solution in the organic phase.

EXAMPLE 3

A mixture of 8.35 parts of mixed dichlorobenzaldehydes, consisting 69.2% of the 2,3-, 2,4- and 2,5- isomers and 30.8% of the 2,6- isomer was dissolved in 48 parts of tetrachloroethylene. A solution of 10.8 parts of sodium bisulfite in 30 parts of water was added, and mixed and the mixture was heated and maintained at about 86° C. for about 30 minutes and then allowed to settle, forming an aqueous phase and a tetrachloroethylene phase. Analysis of the tetrachloroethylene phase indicated about 43% of the starting 2,6- isomer and about 23% of starting mixture of other isomers remained in solution in the organic phase.

EXAMPLE 4

A solution was prepared from 8.05 parts of the dichlorobenzaldehyde mixture of Example 3 and 23 parts of 2,2,4- trimethylpentane. A solution of 9.94 parts of sodium bisulfite in 40 parts of water was added, mixed, and allowed to settle as in Example 3, except that the temperature was maintained at about 83° C. Analysis of the trimethylpentane phase indicated about 18% of the starting 2,6- isomers and about 8% of other isomers remained in solution in the organic phase.

EXAMPLE 5

A solution of 8.12 parts of the dichlorobenzaldehyde mixture of Example 3 in 34 parts of chlorobenzene was treated with a solution of 5.36 parts of sodium bisulfite in 30 parts of water, following the general procedure of Example 3 except that the temperature was maintained at about 87° C. Analysis of the chlorobenzene phase indicated about 68% of the starting 2,6- isomer and about 47% of the starting mixture of other isomers remained in solution therein.

What is claimed is:

1. A process for the separation of 2,6- dichlorobenzaldehyde from mixture of dichlorobenzaldehyde isomers which comprises dissolving the mixture of isomers in a water-immiscible, chemically inert organic solvent, contacting the resultant organic solution with an aqueous sodium bisulfite solution, and separating the resultant aqueous and organic phases.

2. A process according to claim 1 wherein the organic solution and aqueous sodium bisulfite solution are contacted at a temperature of about 50° to about 100° Celsius.

3. A process according to claim 2 wherein the aqueous sodium bisulfite is characterized by a molarity of about 1.0 to about 5.0.

4. A process according to claim 2 wherein the organic solvent is an aromatic hydrocarbon.

5. A process according to claim 2 wherein the organic solvent is an aliphatic hydrocarbon.

6. A process according to claim 2 wherein the organic solvent is a chloro-substituted aromatic hydrocarbon.

7. A process according to claim 2 wherein the organic solvent is a chloro-substituted aliphatic hydrocarbon.

8. A process according to claim 4 wherein the organic solvent is toluene.

9. A process according to claim 5 wherein the organic solvent is 2,2,4-trimethylpentane.

10. A process according to claim 6 wherein the organic solvent is chlorobenzene.

11. A process according to claim 7 wherein the organic solvent is tetrachloroethylene.

12. A process for treating a mixture of isomeric dichlorobenzaldehydes which comprises dissolving the mixture in toluene and contacting the resultant toluene solution with an aqueous sodium bisulfite solution at a temperature of about 50° to about 100° Celsius, to form a toluene phase and an aqueous phase, and recovering from the toluene phase, a dichlorobenzaldehyde composition substantially enriched in 2,6-dichlorobenzaldehyde.